United States Patent [19]
Zaha

[11] Patent Number: 5,149,328
[45] Date of Patent: Sep. 22, 1992

[54] INTRAVENOUS NEEDLE ASSEMBLY HAVING INTERLOCKING WINGS

[75] Inventor: Juergen H. Zaha, Winthrop Harbor, Ill.

[73] Assignee: Abbott Laboratories, Abbott Park, Ill.

[21] Appl. No.: 636,653

[22] Filed: Dec. 31, 1990

[51] Int. Cl.⁵ .............................................. A61M 5/32
[52] U.S. Cl. ..................................... 604/177; 604/174
[58] Field of Search ................................ 604/177, 174

[56] References Cited

U.S. PATENT DOCUMENTS 3,640,275  2/1972  Burke et al. ........................ 604/177
3,670,727  6/1972  Reiterman ........................... 604/177

Primary Examiner—John J. Wilson
Assistant Examiner—Jeffrey A. Smith
Attorney, Agent, or Firm—A. Nicholas Rrausch; Clifford A. Dean

[57] ABSTRACT

A winged needle assembly includes a steel needle, a plastic hub molded to secure a portion of the needle, flexible wings attached to the hub for manual manipulation of the needle, and an interlocking pattern of grooves or ridges on the wing surfaces to prevent relative movement of the wings when flexed together.

2 Claims, 1 Drawing Sheet

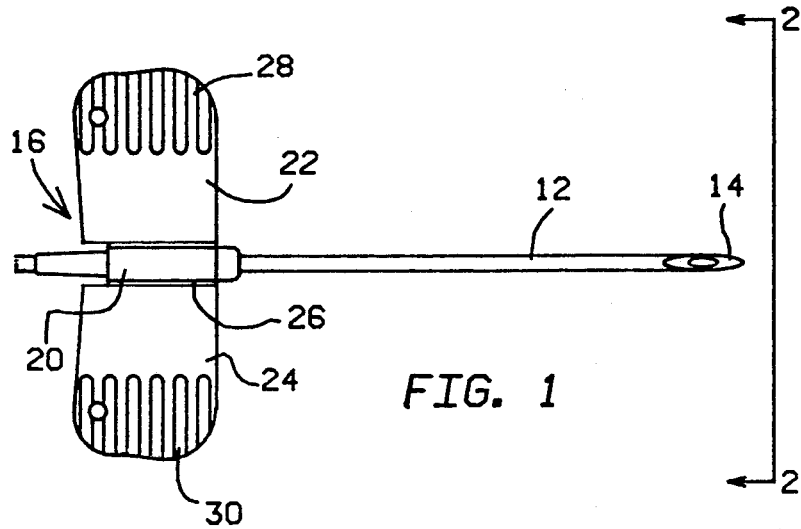
FIG. 1
FIG. 2
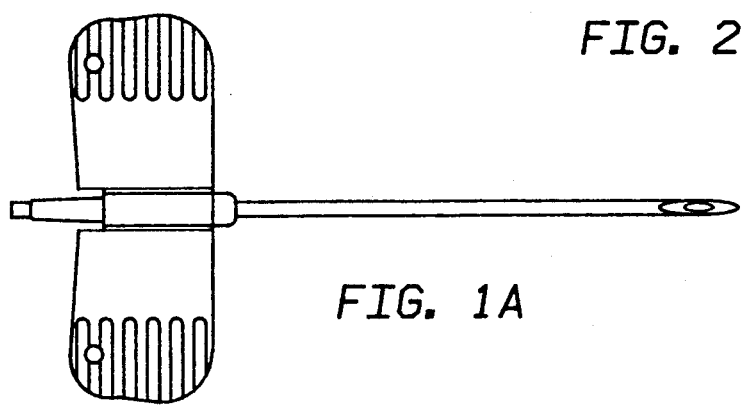
FIG. 1A
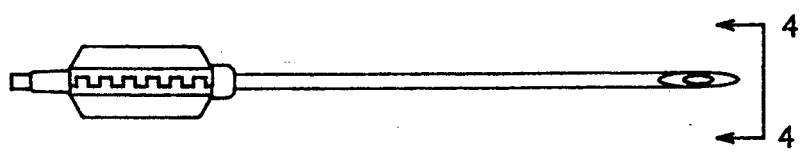
FIG. 3
FIG. 4
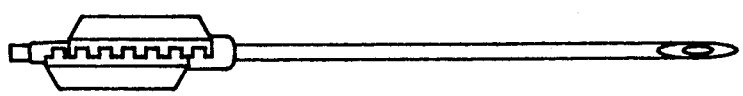
FIG. 5

INTRAVENOUS NEEDLE ASSEMBLY HAVING INTERLOCKING WINGS

BACKGROUND OF THE INVENTION

The present invention relates to a winged needle assembly used for intravenous infusion or catheter placement. More particularly, the invention relates to an assembly for reliably interlocking the wings of the needle assembly during insertion of the needle into the vein of a patient.

Winged infusion sets makes venipuncture easier as suggested by U.S. Pat. No. 3,064,648 to Bujan, hereby incorporated by reference herein. The flexible plastic wings fold or are pinched together for firm needle control during venipuncture and fold flat after needle insertion to provide a firm anchor for taping. The short needle shaft minimizes the possibility of needle movement within the vein.

U.S. Pat. Nos. 4,300,553, 4,388,074 and 4,389,210, each of which is hereby incorporated by reference herein, disclose needle-inside catheter placement assemblies which capture a needle in the winged hub assembly to assist in puncturing a vein and placing a catheter therein. The needle is then withdrawn.

Of prime concern in both procedures is the insertion of the needle into the vein. Care must be taken not to further cut or puncture the sides of the vein. Any movement of the sharp needle tip may cause damage to the patient's vein.

The flexible wings of known winged needle assemblies are capable of flexing so that both wings can be firmly grasped between the thumb and forefinger. However the smooth surfaces of the plastic wings which are pressed together allows the wings to slid against each other. This relative movement of the wings is transferred to the needle shaft and may cause the sharp needle tip to pivot or move. If the needle is in the vein when this movement occurs, the vein walls can be damaged.

The above relative movement of the wings has been partially addressed by the inclusion of mating means such as a pin or knob and a receiving cavity or hole on opposed wings so as to index the two wings to each other. When the wings are flexed together, the pin should register into the hole and secure the two wings into relative position.

However, it has been observed that many times the pin does not find or register with the hole and initially sits on the smooth surface of the wing. Often the pin slips into the hole as the needle is being inserted into the vein, which causes the tip of the needle to move correspondingly. Thus, the above solution does not fully prevent needle movement if the wings are initially misaligned.

SUMMARY OF THE INVENTION

Therefore it is a primary object of this invention to provide a simple and reliable construction for interlocking the flexible wings of a winged needle assembly.

It is a further object to this invention to secure the wings from relative movement even if they are misaligned.

In accordance with these objectives, a plastic hub and flexible wing member is molded with interlocking grooves in the opposed wing surfaces. The grooves interlock when the wings are pinched together, whether the wings are in alignment or not. In the illustrated embodiment the opposed grooves are in offset patterns. In other embodiments, the grooves may be in mirror image patterns. Alternatively, patterns of raised ridges may provide the interlocking means.

Other feature and advantages of the present invention will become readily apparent from the following detailed description, the accompanying drawings, and the appended claims.

BRIEF DESCRIPTION OF THE DRAWINGS

A better understanding of a winged needle assembly will be appreciated by reference to the drawings wherein:

FIG. 1 is a plan view of a winged infusion needle assembly according to the present invention;

FIG. 1A is an alternative embodiment of the present invention;

FIG. 2 is a view along line 2—2 in FIG. 1;

FIG. 3 is a view of the winged infusion needle assembly with the wings flexed together in alignment;

FIG. 4 is an end view along line 4—4 in FIG. 3; and

FIG. 5 is a view similiar to FIG. 3 except the wings are misaligned.

DESCRIPTION OF THE PREFERRED EMBODIMENT

Referring to FIG. 1, a winged infusion set 10 includes a hollow needle 12 preferably made of stainless steel and having a beveled or sharp end 14. The winged plastic member 16 can be made of a suitable flexible plastic such as polyvinyl chloride or other medical grade flexible materials. The winged plastic member includes an axially extending hub portion 20 that surrounds and holds the needle. A pair of oppositely extending winged sections 22 and 24 extend radially from the hub. The wings have a weakened hinge portion 26 near the hub to allow the wings to be folded together for gripping by the thumb and forefinger.

Wings 22 and 24 are formed with opposed patterns of relieved grooves 28 and 30 formed in the ends of the wing tips. The grooves preferably are of an offset pattern as shown in FIG. 1 but could also be formed in a mirror image pattern as shown in FIG. 1A. Alternatively, the pattern could be formed by raised ridges on the surface of the wings.

In use, as shown in FIGS. 3 and 4, the wings are pinched together, and the offset pattern of grooves interlock to prevent relative movement of the wings and thus prevent inadvertent movement of the sharp needle tip in the vein. Even if the wings are misaligned as shown in FIG. 5, the wings are prevented from moving relatively to one another. This interlocking feature reduces the potential for damage to the vein wall by inadvertent needle movement.

The foregoing invention can now be practiced by those skilled in the art. Such skilled persons will appreciate that the winged needle assembly of the present invention is not necessarily restricted to the particular preferred embodiments presented herein. For example, as previously discussed, the wings could also be used with needle-inside catheter placement assemblies. The scope of the invention is to be defined by the terms of the following claims in the spirit and meaning of the preceding description.

What is claimed is:

1. A winged needle assembly comprising:
    a steel needle;

a plastic hub molded to secure a portion of the needle:
flexible wings radially attached to the hub for manual manipulation of the needle: and
opposed mirror image patterns of grooves on said flexible wings for interlocking opposed wings to each other when said wings are flexed together to prevent relative movement of said needle.

2. A winged needle assembly comprising:

a steel needle:
a plastic hub molded to secure a portion of the needle:
flexible wings radially attached to the hub for manual manipulation of the needle: and
opposed mirror image patterns of raised ridges on said flexible wings for interlocking opposed wings to each other when said wings are flexed together to prevent relative movement of said needle.

* * * * *